United States Patent
Taber

(10) Patent No.: US 8,083,749 B2
(45) Date of Patent: Dec. 27, 2011

(54) METHOD AND APPARATUS FOR PERFORMING AN OPEN WEDGE, LOW FEMORAL OSTEOTOMY

(75) Inventor: Justin R. Taber, Boulder, CO (US)

(73) Assignee: Arthrex, Inc., Naples, FL (US)

( * ) Notice: Subject to any disclaimer, the term of this patent is extended or adjusted under 35 U.S.C. 154(b) by 895 days.

(21) Appl. No.: 11/998,882

(22) Filed: Dec. 3, 2007

(65) Prior Publication Data

US 2008/0243257 A1    Oct. 2, 2008

Related U.S. Application Data

(60) Provisional application No. 60/872,116, filed on Dec. 1, 2006.

(51) Int. Cl.
*A61B 17/90* (2006.01)

(52) U.S. Cl. .......................... 606/96; 606/88

(58) Field of Classification Search .......... 606/64, 606/88, 87, 96; 623/20.14, 20.16, 20.17
See application file for complete search history.

(56) References Cited

U.S. PATENT DOCUMENTS

| | | |
|---|---|---|
| 2,737,724 A | 3/1956 | Herz |
| 3,579,777 A | 5/1971 | Milewski |
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,523,587 A | 6/1985 | Frey |
| 4,563,489 A | 1/1986 | Urist |
| 4,565,191 A | 1/1986 | Slocum |
| 4,622,959 A * | 11/1986 | Marcus ................ 606/64 |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |

(Continued)

FOREIGN PATENT DOCUMENTS

EP    1669033    6/2006

(Continued)

OTHER PUBLICATIONS

Oliver C. Kessler et al., Avoidance of Medial Cortical Fracture in High Tibial Osteotomy: Improved Technique, Clinical Orthopaedics and Related Research, Feb. 2002, pp. 180-185, No. 395.

*Primary Examiner* — Thomas C. Barrett
*Assistant Examiner* — Christian Sevilla
(74) *Attorney, Agent, or Firm* — Dickstein Shapiro LLP

(57) ABSTRACT

Apparatus for performing an open wedge, low femoral osteotomy, the apparatus comprising an osteotomy guide, a hinge pin and an osteotomy implant, the osteotomy guide comprising: anterior and posterior tissue shields having (i) openings for receiving the hinge pin and defining the hinge pin axis, and (ii) profiles configured to enable fluoroscopic alignment of the hinge pin axis parallel to the sagittal plane of the patient, a cutting guide comprising a cutting slot for defining a cutting plane extending parallel to, and through, the hinge pin axis, and a drill guide comprising a hole for forming a guide hole in the femur which extends substantially perpendicular to the cutting plane, the hinge pin comprising an elongated body, and the osteotomy implant for positioning in a wedge-shaped opening formed about the cutting plane and for receiving a screw extending through the guide hole.

11 Claims, 15 Drawing Sheets

U.S. PATENT DOCUMENTS

| | | |
|---|---|---|
| 4,852,558 A | 8/1989 | Outerbridge |
| 4,936,844 A | 6/1990 | Chandler et al. |
| 5,053,039 A | 10/1991 | Hofmann et al. |
| 5,254,119 A | 10/1993 | Schreiber |
| 5,275,603 A | 1/1994 | Ferrante et al. |
| 5,297,538 A | 3/1994 | Daniel |
| 5,306,276 A | 4/1994 | Johnson et al. |
| 5,352,229 A | 10/1994 | Goble et al. |
| 5,413,579 A | 5/1995 | Du Toit |
| 5,445,640 A | 8/1995 | Johnson et al. |
| 5,451,228 A | 9/1995 | Johnson et al. |
| 5,540,695 A | 7/1996 | Levy |
| 5,569,250 A | 10/1996 | Sarver et al. |
| 5,601,565 A | 2/1997 | Huebner |
| 5,609,635 A | 3/1997 | Michelson |
| 5,613,969 A | 3/1997 | Jenkins, Jr. |
| 5,620,448 A * | 4/1997 | Puddu ............... 606/87 |
| 5,640,813 A | 6/1997 | Glazik et al. |
| 5,662,655 A | 9/1997 | Laboureau et al. |
| 5,669,909 A | 9/1997 | Zdeblick et al. |
| 5,674,296 A | 10/1997 | Bryan et al. |
| 5,681,316 A | 10/1997 | DeOrio et al. |
| 5,722,978 A | 3/1998 | Jenkins, Jr. |
| 5,733,290 A | 3/1998 | McCue et al. |
| 5,749,875 A | 5/1998 | Puddu |
| 5,766,251 A | 6/1998 | Koshino |
| 5,843,085 A | 12/1998 | Graser |
| 5,888,223 A | 3/1999 | Bray, Jr. |
| 5,911,724 A | 6/1999 | Wehrli |
| 5,980,526 A | 11/1999 | Johnson et al. |
| 6,008,433 A | 12/1999 | Stone |
| 6,027,504 A | 2/2000 | McGuire |
| 6,039,761 A | 3/2000 | Li et al. |
| 6,086,593 A | 7/2000 | Bonutti |
| 6,099,531 A | 8/2000 | Bonutti |
| 6,102,950 A | 8/2000 | Vaccaro |
| 6,190,390 B1 | 2/2001 | McAllister |
| 6,200,347 B1 | 3/2001 | Anderson et al. |
| 6,203,546 B1 | 3/2001 | MacMahon |
| 6,224,599 B1 | 5/2001 | Baynham et al. |
| 6,277,149 B1 | 8/2001 | Boyle et al. |
| 6,287,308 B1 | 9/2001 | Betz et al. |
| 6,379,361 B1 | 4/2002 | Beck, Jr. et al. |
| 6,423,063 B1 | 7/2002 | Bonutti |
| 6,461,359 B1 | 10/2002 | Tribus et al. |
| 6,478,800 B1 | 11/2002 | Fraser et al. |
| 6,565,570 B2 | 5/2003 | Sterett et al. |
| 6,575,982 B1 | 6/2003 | Bonutti |
| 6,755,841 B2 | 6/2004 | Fraser et al. |
| 6,796,986 B2 | 9/2004 | Duffner |
| 6,823,871 B2 | 11/2004 | Schmieding |
| 2002/0010513 A1 | 1/2002 | Schmieding |
| 2002/0029084 A1 | 3/2002 | Paul et al. |
| 2002/0095156 A1 | 7/2002 | Kuras et al. |
| 2003/0028197 A1 | 2/2003 | Hanson et al. |
| 2003/0105526 A1 | 6/2003 | Bryant et al. |
| 2003/0171757 A1 | 9/2003 | Coon et al. |
| 2003/0195516 A1 | 10/2003 | Sterett et al. |
| 2003/0199881 A1 | 10/2003 | Bonutti |
| 2004/0039387 A1 | 2/2004 | Gause et al. |
| 2005/0075641 A1 | 4/2005 | Singhatat et al. |
| 2005/0216090 A1 | 9/2005 | O'Driscoll et al. |
| 2005/0228498 A1 | 10/2005 | Andres |
| 2005/0251147 A1 | 11/2005 | Novak |
| 2005/0273114 A1 | 12/2005 | Novak |
| 2005/0273115 A1 | 12/2005 | Coon et al. |
| 2006/0106396 A1 | 5/2006 | Justin et al. |
| 2006/0122617 A1 | 6/2006 | Lavallee et al. |
| 2006/0129163 A1 | 6/2006 | McGuire |
| 2006/0149274 A1 | 7/2006 | Justin et al. |
| 2006/0149275 A1 | 7/2006 | Cadmus |
| 2006/0241636 A1 * | 10/2006 | Novak et al. ............ 606/87 |

FOREIGN PATENT DOCUMENTS

| | | |
|---|---|---|
| FR | 2741525 | 5/1997 |
| WO | WO 2005/048888 | 6/2005 |
| WO | WO 2006/107800 | 10/2006 |

* cited by examiner

TISSUE SHIELDS IN PLACE

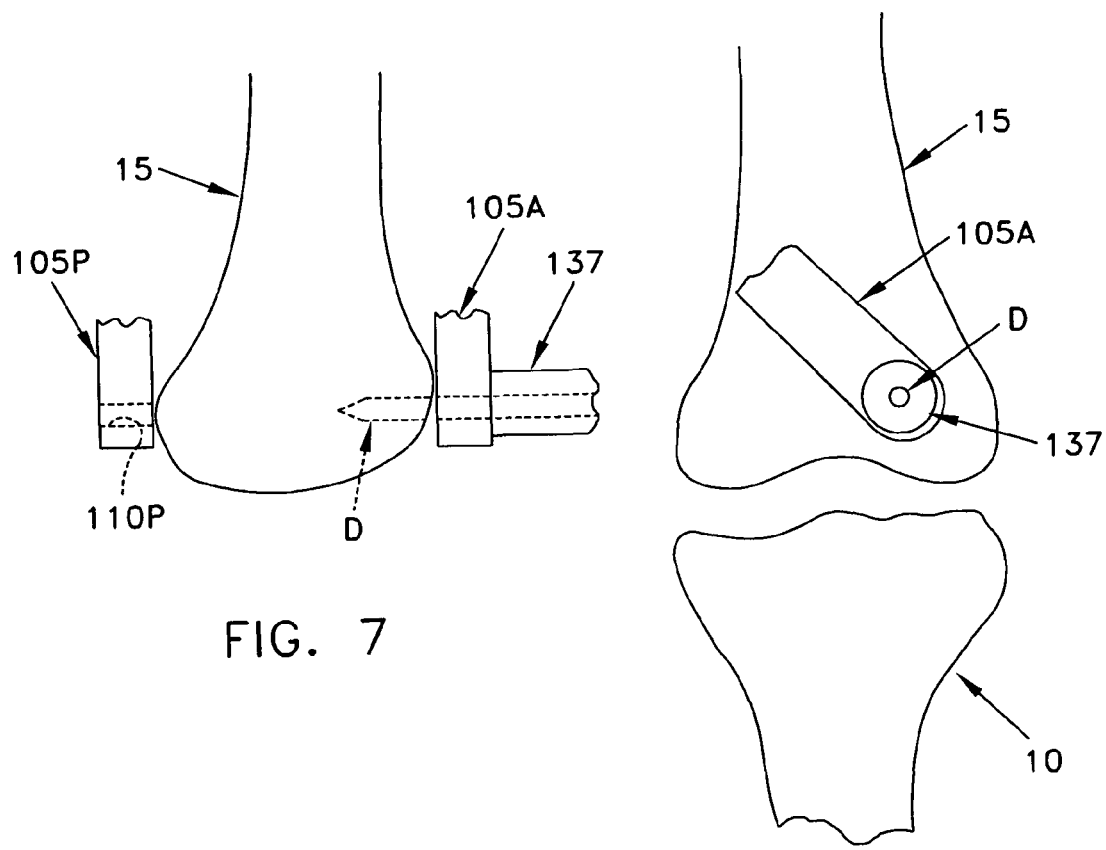

OPEN FEMUR TO PRODUCE
WEDGE-LIKE OPENING IN FEMUR

INSTALL OSTEOTOMY IMPLANT IN
WEDGE-LIKE OPENING IN FEMUR

COMPLETE BORES INTO FEMUR ON
FAR SIDE OF IMPLANT

INSTALL COMPRESSION SCREWS TO
SECURE OSTEOTOMY IMPLANT IN
WEDGE-LIKE OPENING IN FEMUR

METHOD AND APPARATUS FOR PERFORMING AN OPEN WEDGE, LOW FEMORAL OSTEOTOMY

REFERENCE TO PENDING PRIOR PATENT APPLICATION

This patent application claims benefit of pending prior U.S. Provisional Patent Application Ser. No. 60/872,116, filed Dec. 1, 2005 by Justin R. Taber for METHOD, INSTRUMENTATION AND FIXATION FOR LATERAL OPENING WEDGE OSTEOTOMY OF THE DISTAL FEMUR, which patent application is hereby incorporated herein by reference.

FIELD OF THE INVENTION

This invention relates to surgical methods and apparatus in general, and more particularly to surgical methods and apparatus for performing open wedge osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to the relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which the load is transferred across the knee joint.

There are essentially two ways in which to adjust the orientation of the tibia: (i) the closed wedge technique; and (ii) the open wedge technique.

With the closed wedge technique, a wedge of bone is removed from the upper portion of the tibia, and then the tibia manipulated so as to close the resulting gap, whereby to reorient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to reorient the lower portion of the tibia relative to the tibial plateau and hence adjust the manner in which load is transferred from the femur to the tibia.

As noted above, it is also possible to modify the geometry of the femur, so as to adjust the manner in which load is transferred across the knee joint.

The present invention is directed to open wedge osteotomies of the femur.

SUMMARY OF THE INVENTION

The present invention comprises a novel method and apparatus for performing an open wedge, low femoral osteotomy. More particularly, the present invention comprises the provision and use of a novel method and apparatus for forming an appropriate osteotomy cut into the lower portion of the femur, manipulating the femur so as to open an appropriate wedge-like opening in the femur, and then inserting an appropriate wedge-shaped implant into the wedge-like opening in the femur, so as to stabilize the femur with the desired orientation, whereby to reorient the lower portion of the femur relative to the tibia and hence adjust the manner in which load is transferred from the femur to the tibia.

In one form of the present invention, there is provided apparatus for performing an open wedge, low femoral osteotomy, the apparatus comprising:

an osteotomy guide, a hinge pin and an osteotomy implant;
the osteotomy guide comprising:
anterior and posterior tissue shields, wherein the distal ends of the anterior and posterior tissue shields comprise openings for receiving the hinge pin and defining the hinge pin axis, and further wherein the proximal ends of the anterior and posterior tissue shields comprise profiles configured to enable fluoroscopic alignment of the hinge pin axis parallel to the saggital plane of the patient;
a cutting guide and a drill guide connected to the proximal ends of the anterior and posterior tissue shields, wherein the cutting guide comprises a cutting slot for defining a cutting plane extending parallel to, and through, the hinge axis, and further wherein the drill guide comprises a drill guide hole for forming a guide hole in the femur, wherein the guide hole extends substantially perpendicular to the cutting plane;
the hinge pin comprising an elongated body sized to be received in the openings in the distal ends of the anterior and posterior tissue shields; and
an osteotomy implant for positioning in a wedge-shaped opening formed in the femur about the cutting plane and for receiving a screw extending through the guide hole.

In another form of the invention, there is provided a method for performing an open wedge, low femoral osteotomy, the method comprising:

deploying a hinge pin within the femur so that the hinge pin extends anterior-to-posterior, parallel to the sagittal plane of the patient;

forming an osteotomy cut through the femur, wherein the osteotomy cut extends parallel to, substantially contacts, the hinge pin;

opening the femur along the osteotomy cut so as to form a wedge-shaped opening in the femur;

positioning an osteotomy implant within the wedge-shaped opening in the femur.

BRIEF DESCRIPTION OF THE DRAWINGS

These and other objects and features of the present invention will be more fully disclosed or rendered obvious by the following of the preferred embodiments of the invention, which is to be considered together with the accompanying drawings wherein like numbers refer to like parts, and further wherein:

FIGS. 4-24 are schematic views illustrating an open wedge, low femoral osteotomy performed in accordance with the present invention.

DETAILED DESCRIPTION OF THE PREFERRED EMBODIMENTS

Figure 2:
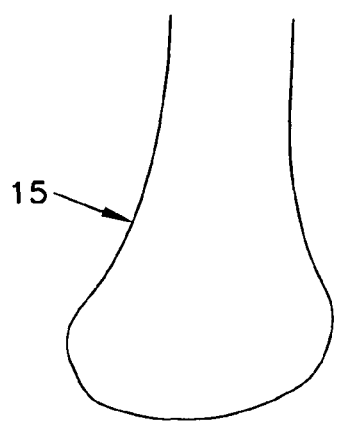
FIGS. 1 and 2 are schematic views showing the tibia and femur of a knee joint.
Figure 1:
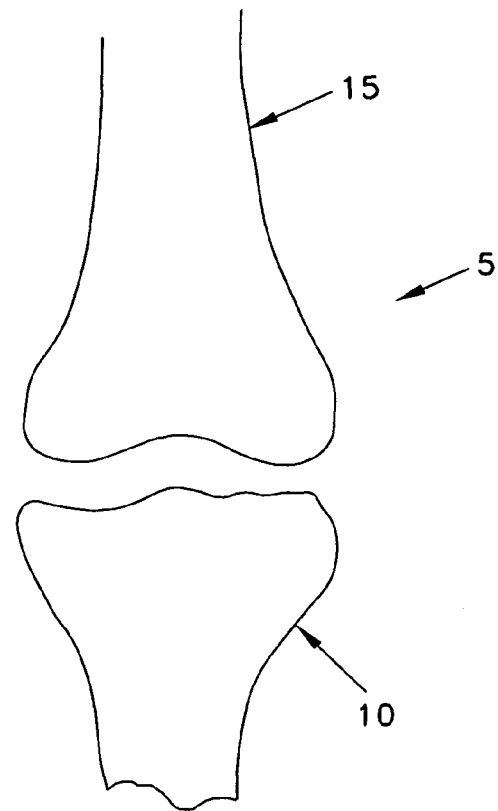

Looking first at FIGS. 1 and 2, there is shown a knee joint 5 upon which an open wedge, low femoral osteotomy is to be performed. Knee joint 5 generally comprises a tibia 10 and a femur 15.

Figure 3:
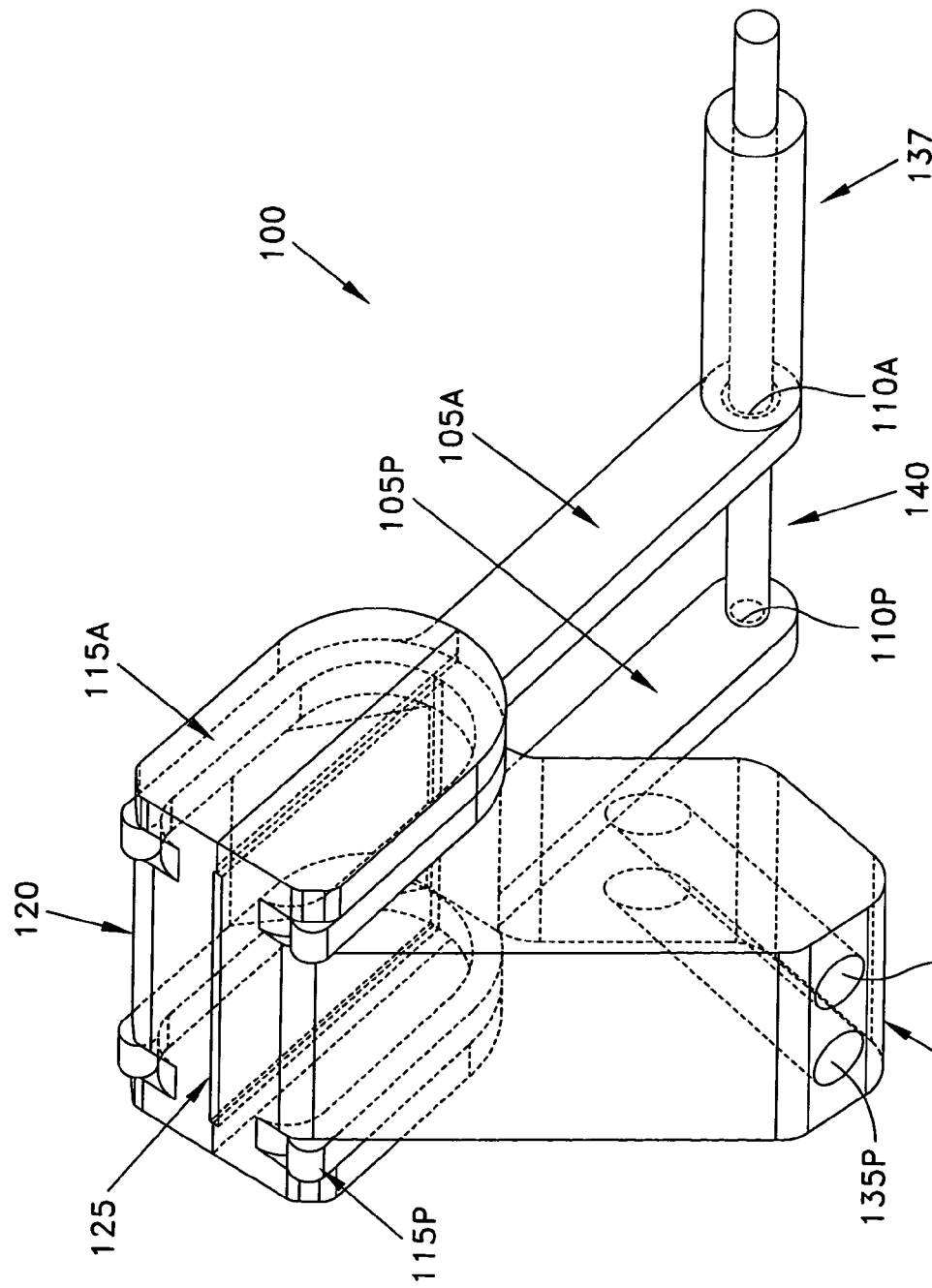
FIG. 3 is a schematic view of an osteotomy guide which may be used to perform an open-wedge, low femoral osteotomy in accordance with the present invention.
Figures 4, 5:
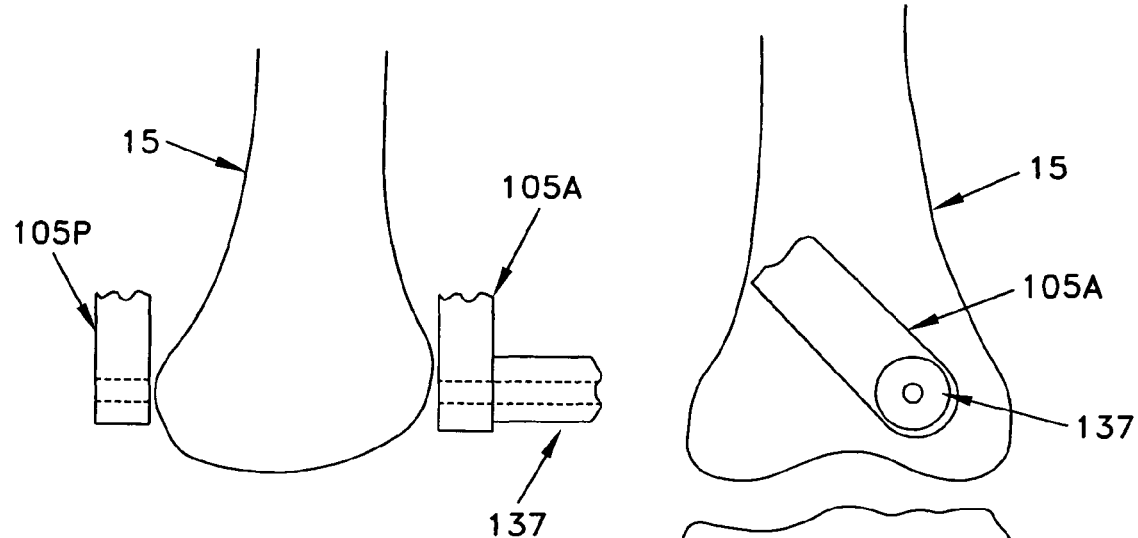
Figures 8, 9:
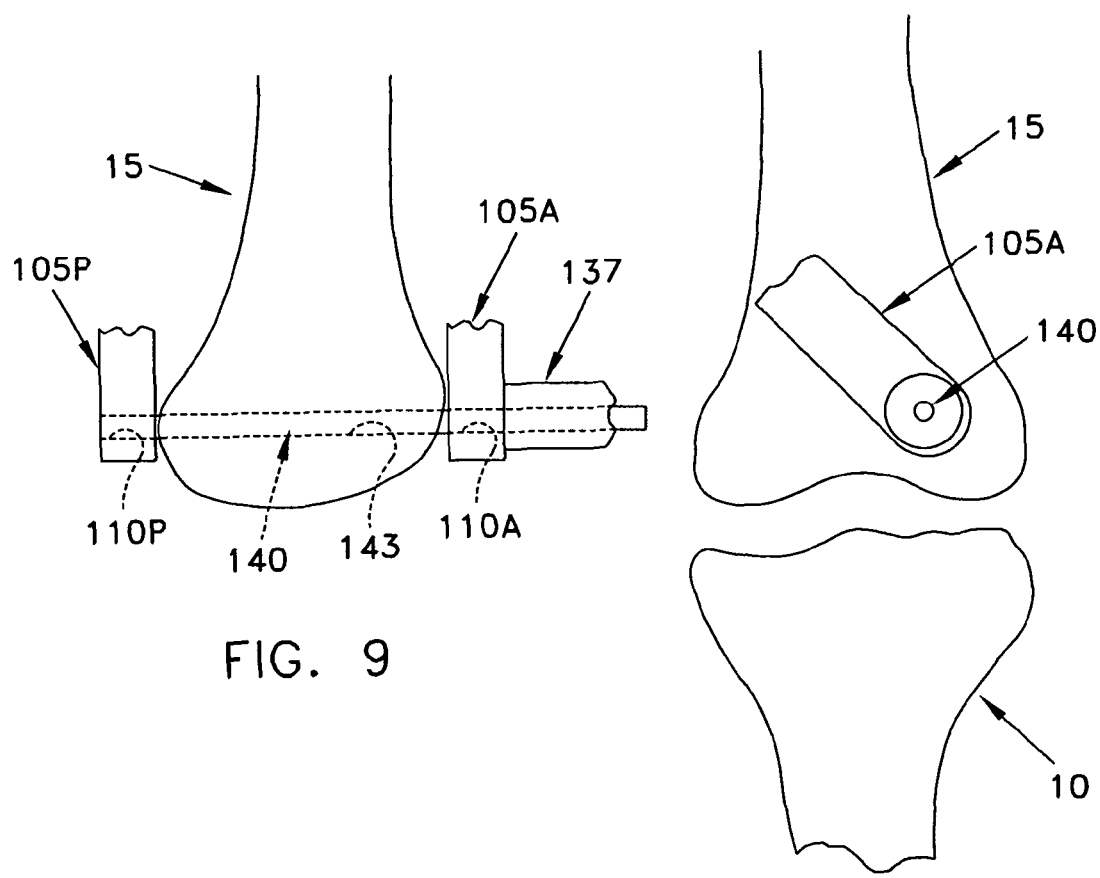
Figure 10:
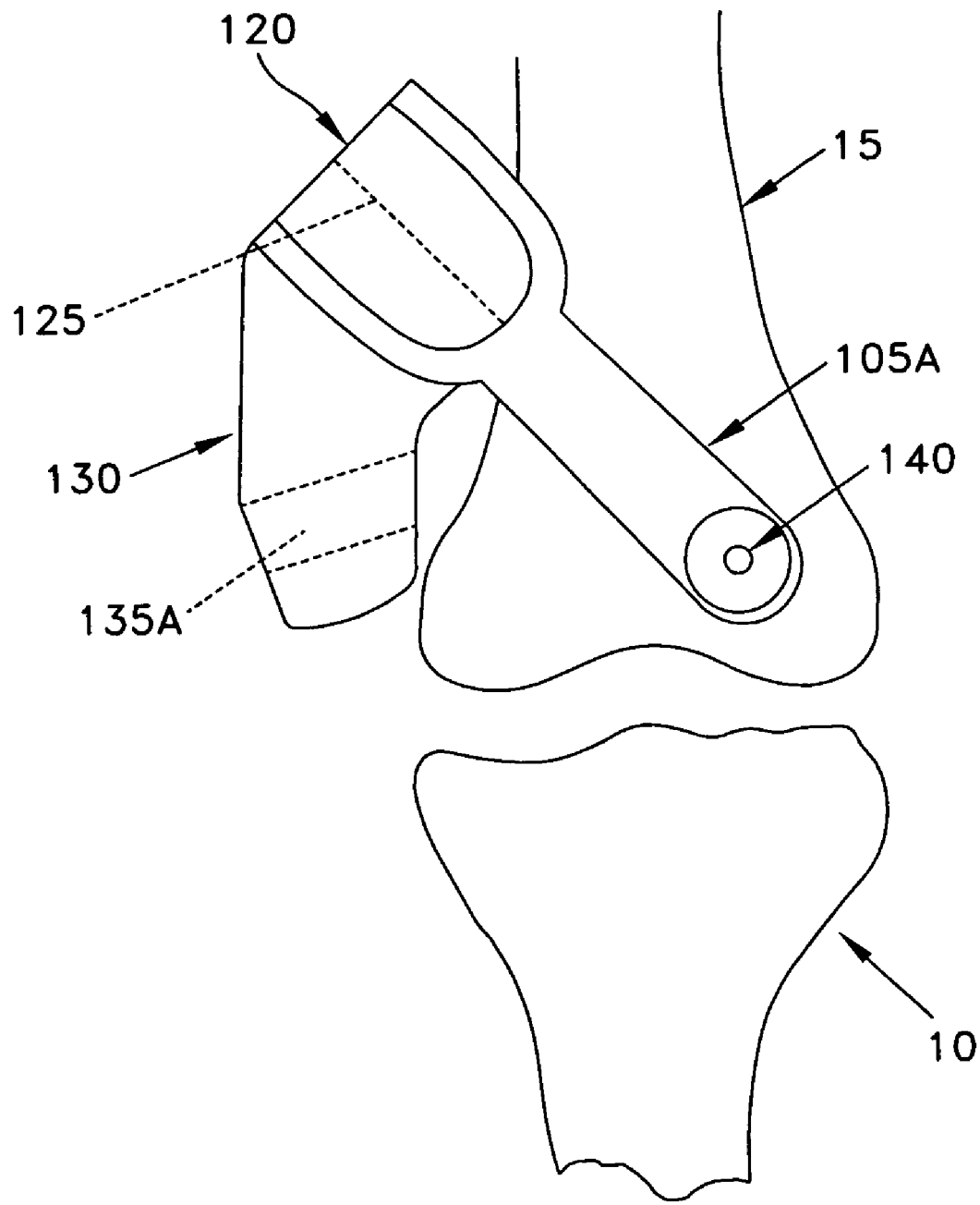

In accordance with the present invention, the open wedge, low femoral osteotomy is preferably performed using the osteotomy guide 100 shown in FIG. 3. Osteotomy guide 100 generally comprises an anterior tissue shield 105A having a hole 110A formed on one end thereof and a wishbone segment 115A formed on the other end thereof; a posterior tissue shield 105P having a hole 110P formed on one end thereof and a wishbone segment 115P formed on the other end thereof; a cutting guide 120 having a cutting slot 125 formed therein and a drill guide 130 having a pair of drill guide holes 135A and 135P formed therein, with cutting guide 120 and drill guide 130 being formed so as to mount to wishbone segments 115A, 115P of tissue shields 105A, 105P; a guide bushing 137 for mounting to anterior tissue shield 105A; and a hinge pin 140.

Looking next at FIGS. 4-24, the open wedge, low femoral osteotomy is preferably performed as follows.

(1) First, using a fluoroscope set up in Anterior-Posterior (AP) view, the desired location of the osteotomy hinge is marked on the skin (not shown).

(2) Next, a lateral incision (also not shown) is made in the skin and then anterior tissue shield 105A and posterior tissue shield 105P are inserted, anteriorly and posteriorly, respectively, alongside femur 15. See FIGS. 4 and 5.

(3) Next, cutting guide 120 and drill guide 130 are snapped into wishbone segments 115A, 115P of tissue shields 105A, 105P, so that tissue shields 105A, 105P, cutting guide 120 and drill guide 130 assume the configuration shown in FIG. 3.

(4) Then an incision is made at the boney hinge tissue mark and guide bushing 137 is mounted into hole 110A in anterior tissue shield 105A. See FIGS. 4 and 5.

(5) Next, the desired location of the hinge pin boney entrance is marked by drilling approximately 5 mm into the bone with a hinge pin drill D. See FIGS. 6 and 7. This forms a pivot point for hinge pin drill D in the following alignment step (Step 6) which will determine the orientation of the hinge pin hole.

(6) During the alignment step, the surgeon holds hinge pin drill D and an alignment handle (not shown) connected to osteotomy guide 100, pushing a reference edge on cutting guide 120 against the lateral aspect of the femur. The surgeon's other hand holds hinge pin drill D in the boney pivot created in the preceding step (Step 5). Looking in the lateral fluoroscope view, the hinge pin axis is made parallel with the patient's sagittal plane by aligning the arms of the two wishbones 115A, 115P in the fluoroscope view.

(7) When the aforementioned alignment is achieved, a hinge pin hole 143 (FIGS. 9 and 14) is drilled into the femur, using hinge pin drill D. On account of the foregoing procedure, the hinge pin hole will extend anterior-to-posterior, parallel with the patient's sagittal plane.

(8) Next, hinge pin 140 is inserted into hinge pin hole 143, passing through guide bushing 137, through anterior tissue shield 105A and threading into hole 110P in posterior tissue shield 105P. See FIGS. 8 and 9. A collet nut (not shown) may be used to lock guide bushing 137 and hinge pin 140 together.

Figure 11:
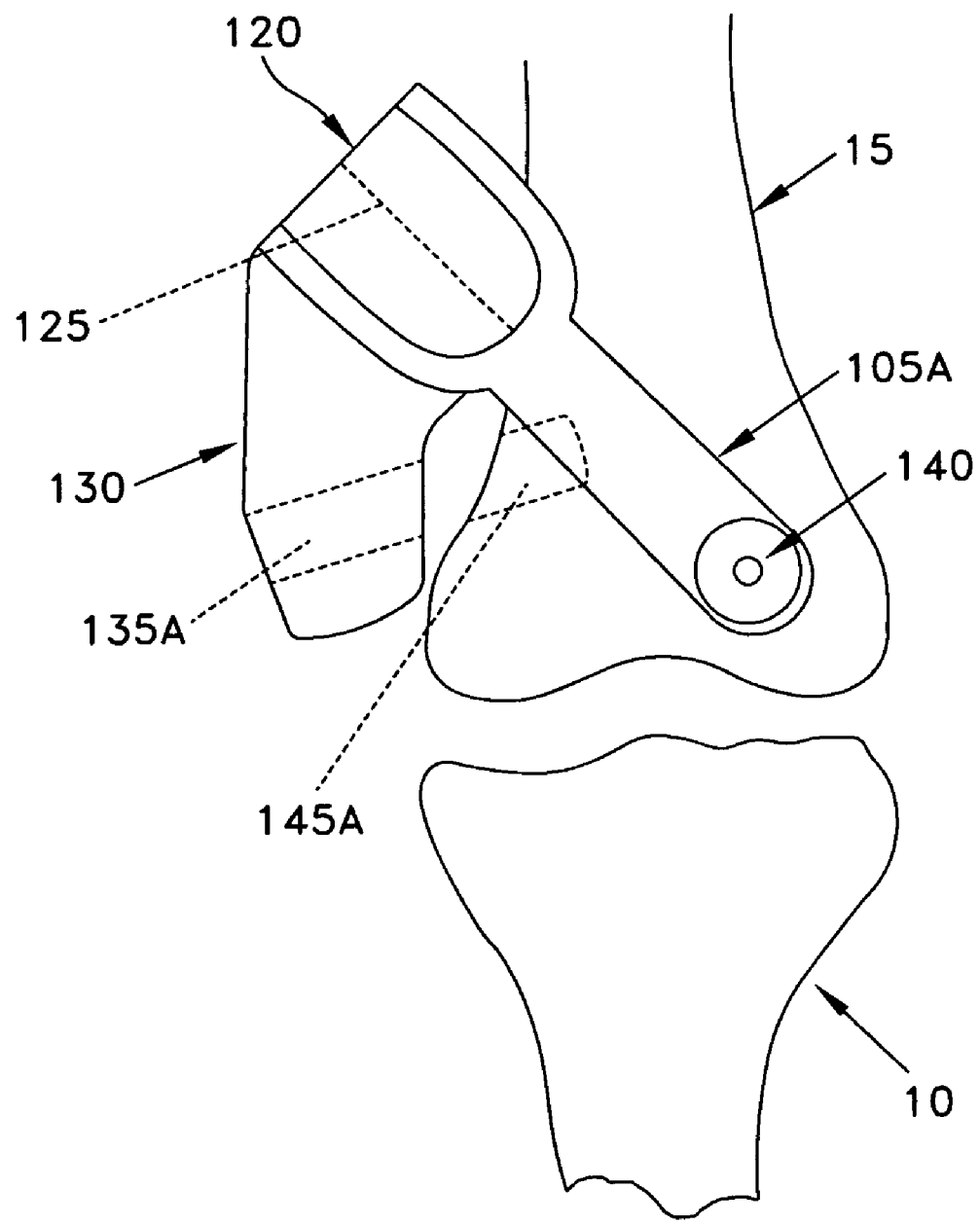
Figure 12:
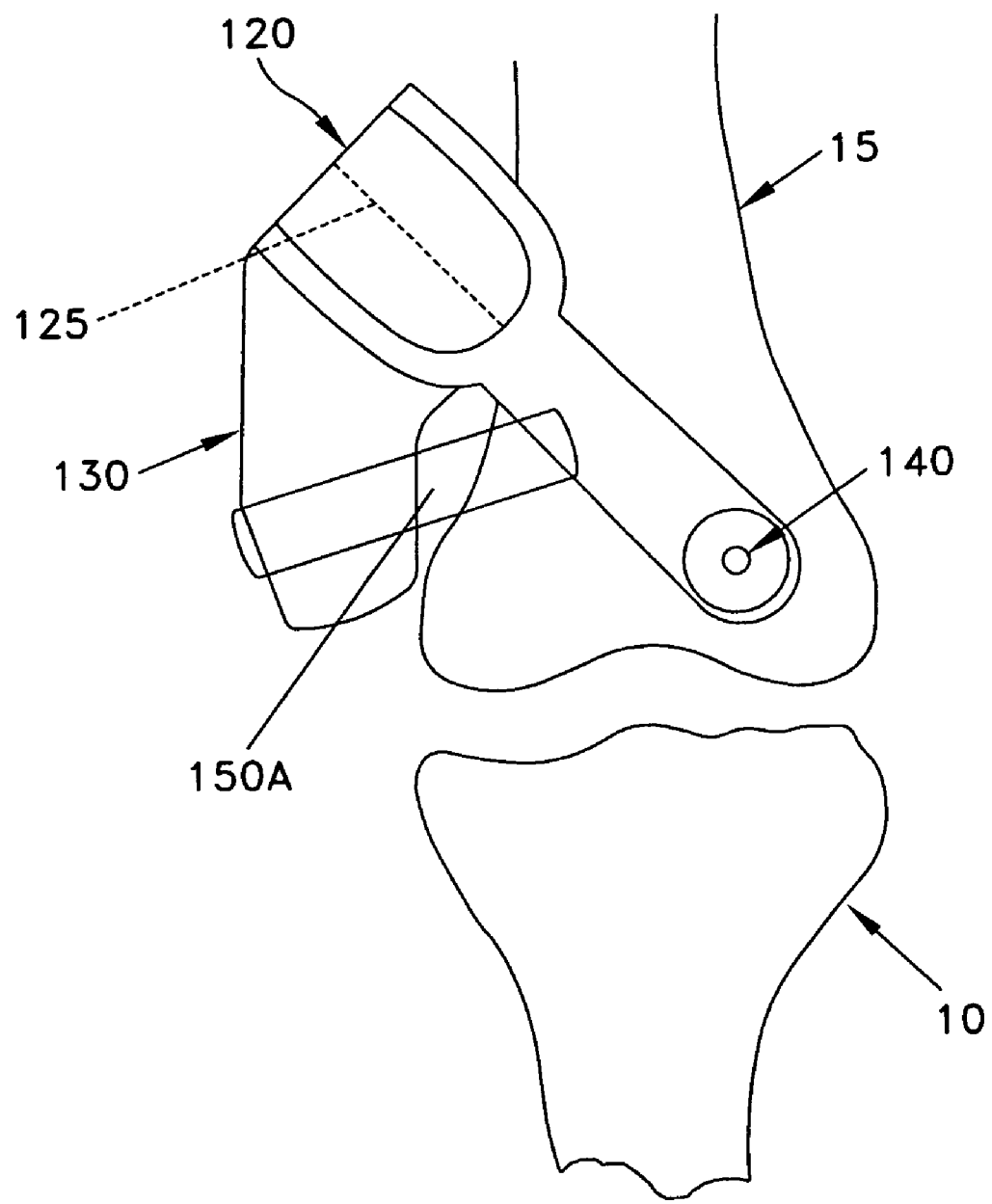
Figure 13:
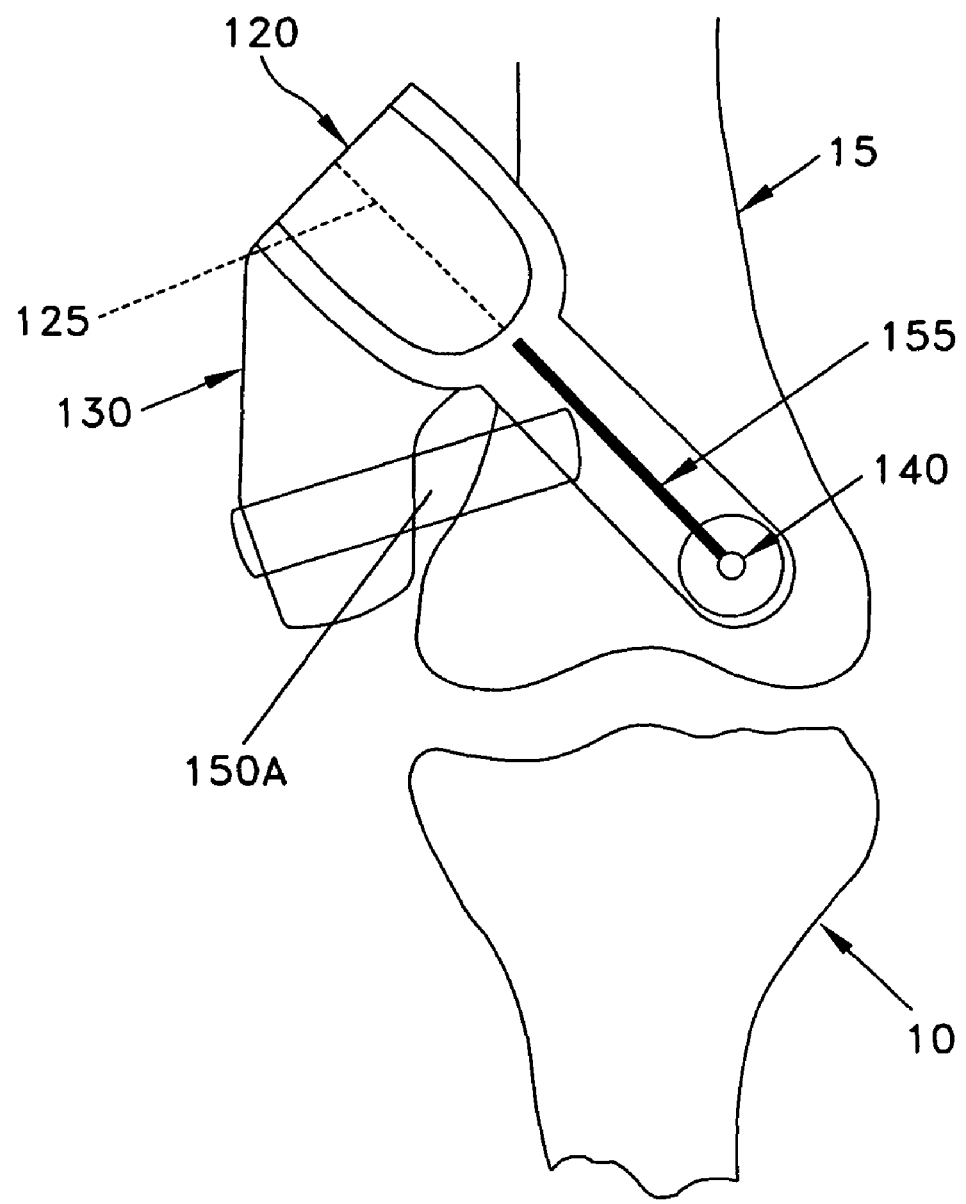
Figure 14:
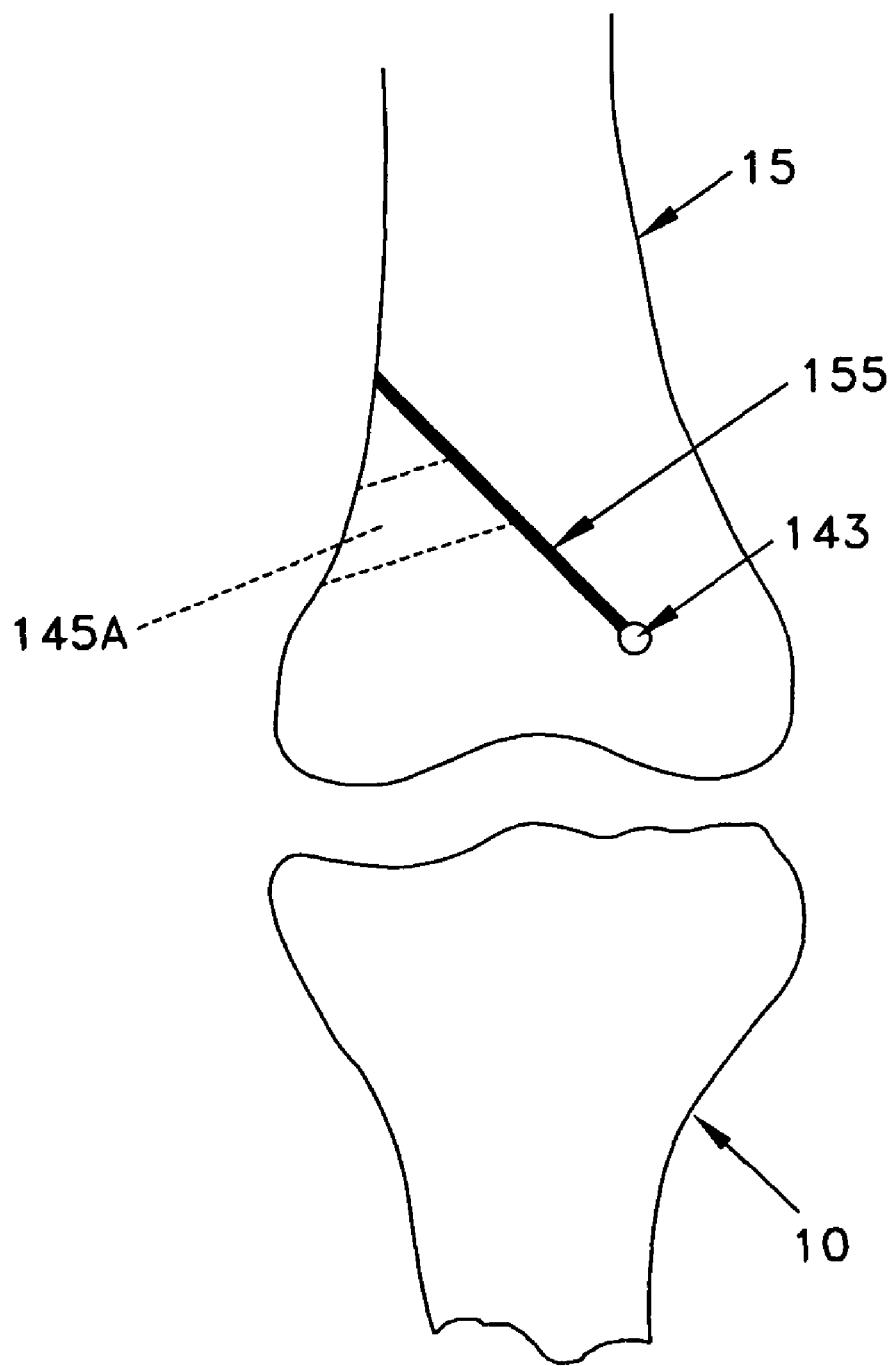
Figure 16:
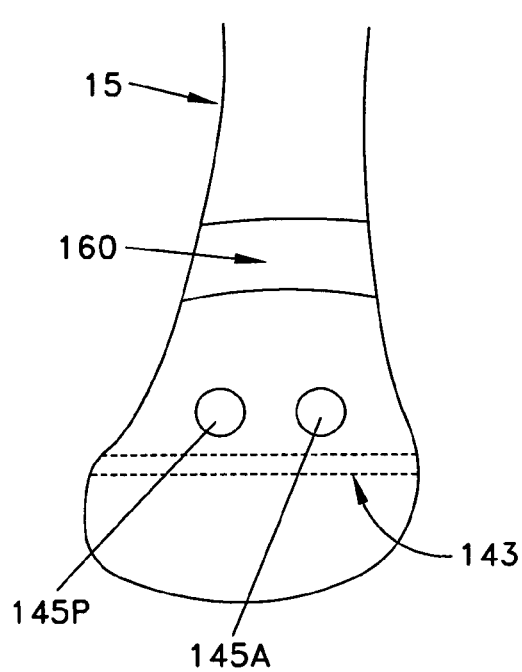
Figure 15:
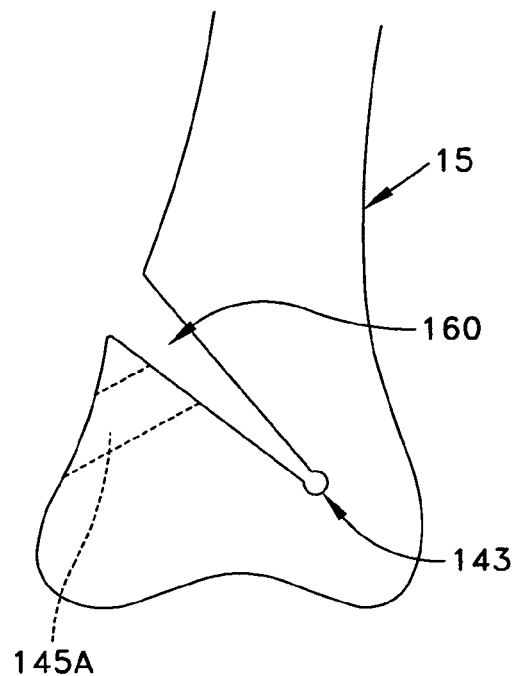

(9) A reference edge of drill guide 130 is pushed up against the lateral aspect of the femur (see FIG. 10) and then two guide holes 145A, 145P are drilled through drill guide holes 135A, 135P, respectively. Guide holes 145A, 145P are drilled up to the osteotomy plane. See FIG. 11. Note that only drill guide hole 135A, and only guide hole 145A, are shown in FIG. 11 due to the angle of view.

(10) Next, two bolts 150A, 150P, equipped with self-cutting threads (to form threads in the femur, to be used later by compression screws, as will hereinafter be discussed) are inserted into the drill guide holes 135A, 135P and into guide holes 145A, 145P, respectively, tightening the instrumentation against the bone. See FIG. 12.

(11) Then an oscillating saw blade (not shown) is advanced through cutting slot 125 in cutting guide 120 and into the femur. Cutting slot 125 guides the oscillating saw blade so as to restrict the osteotomy cut 155 (FIG. 13) to the zone within the "safety cage" formed by anterior and posterior tissue shields 105A, 105P and hinge pin 140. As a result, the delicate vascular and neurological tissues surrounding the knee joint are fully protected during formation of osteotomy cut 155.

(12) At this point, bolts 150A, 150P are withdrawn from the femur, hinge pin 140 is withdrawn from the femur, and the remainder of osteotomy guide 5 is removed from the surgical site, leaving osteotomy cut 155 extending from the surface of the femur to hinge pin hole 143, with guide holes 145A, 145P extending to osteotomy cut 155. See FIG. 14.

(13) Next, the femur is opened along osteotomy cut 155, so as to create a wedge-like opening 160 in the lower end of the femur. See FIGS. 15 and 16.

Figure 17:
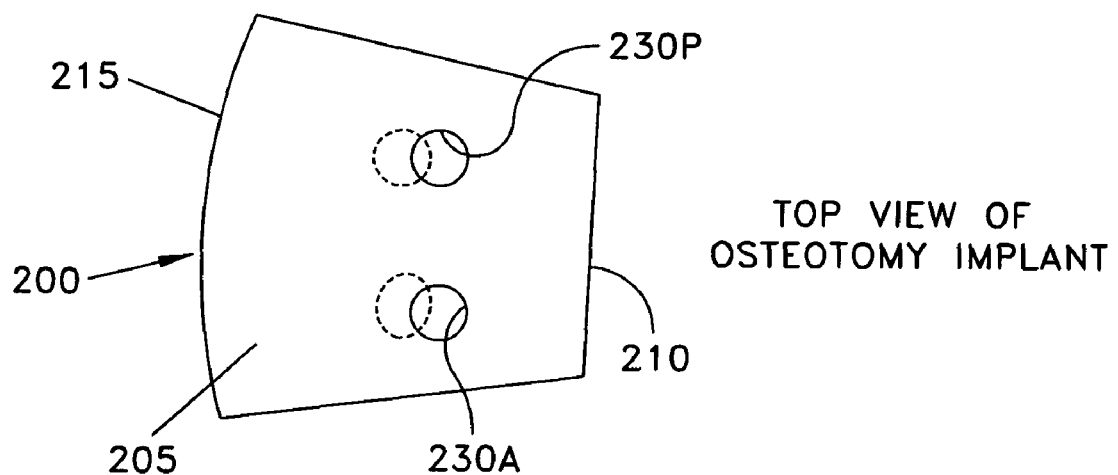
Figure 18:
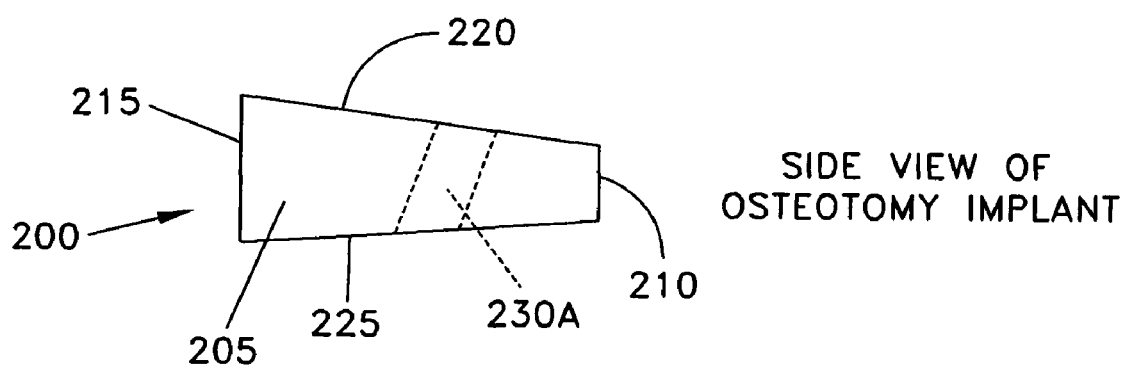
Figure 20:
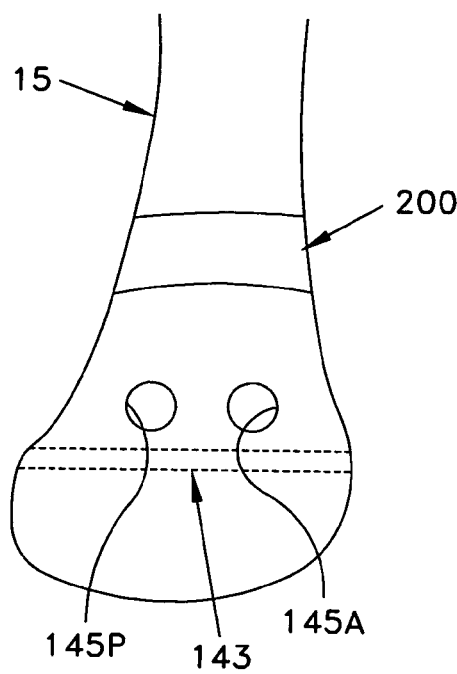
Figure 19:
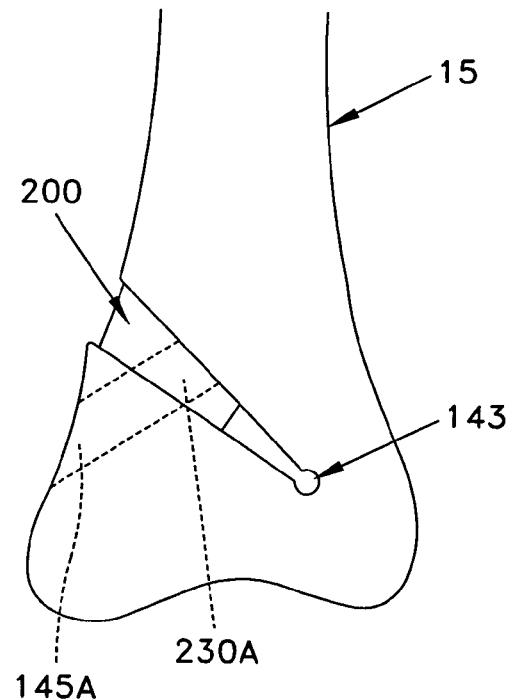
Figure 22:
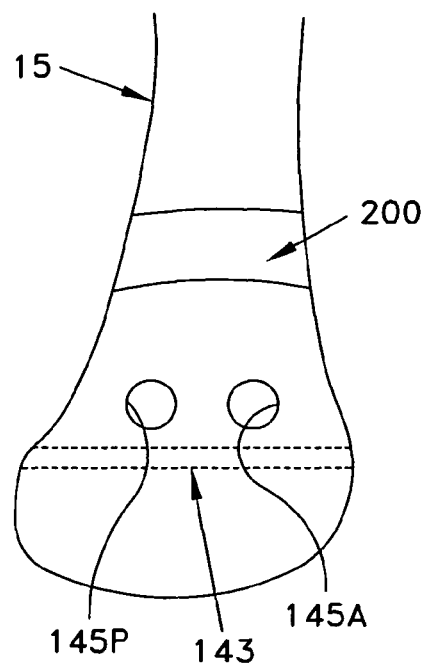

(14) Then an appropriate wedge-shaped implant is disposed in wedge-like opening 160 so as to maintain the femur in its proper disposition during healing. Preferably the wedge-shaped implant 200 shown in FIGS. 17 and 18 is used. Wedge-shaped implant 200 generally comprises a wedge-shaped body 205 having a distal end 210 and a proximal end 215, with an upper surface 220 and a lower surface 225. A pair of holes 230A, 230P extend through body 205, from lower surface 225 to upper surface 220. As seen in FIGS. 19 and 20, wedge-shaped implant 200 is positioned in wedge-shaped opening 160 so that the implant's upper surface 220 engages the upper portion of the femur and the implant's lower surface 225 engages the lower portion of the femur, and so that implant holes 230A, 230P are aligned with guide holes 145A, 145P, respectively.

Figure 21:
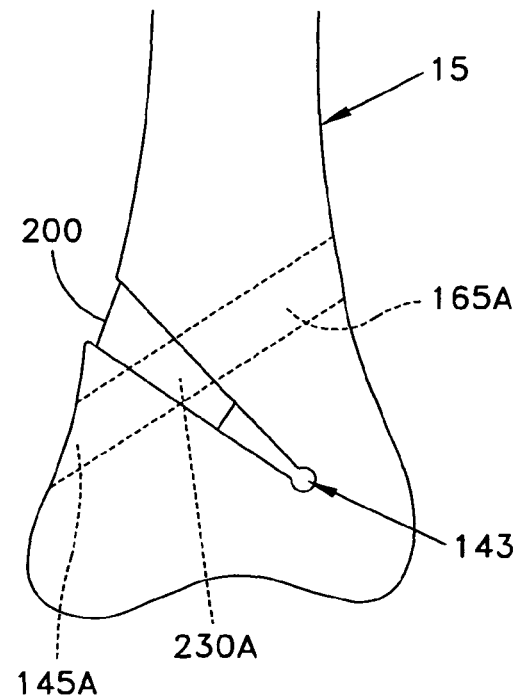
Figure 24:
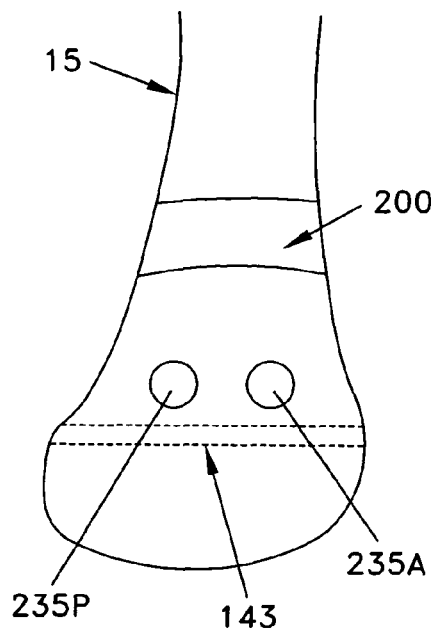

(15) Next, a pair of extension holes 165A, 165P are drilled into the femur on the far side of the implant, with extension hole 165A being aligned with implant hole 230A and guide hole 145A, and with extension hole 165P being aligned with implant hole 230P and guide hole 145P. See FIGS. 21 and 22. Note that only extension hole 165A, and only guide hole 154A, are shown in FIG. 21 due to the angle of view.

Figure 23:
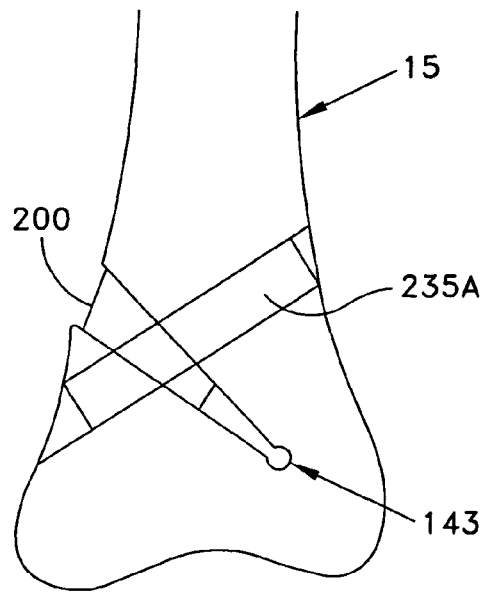

(16) Finally, wedge-shaped implant 200 is secured in position by passing a compression screw 235A through guide hole 145A, implant hole 230A and extension hole 165A, and by passing a compression screw 235P through guide hole 145P, implant hole 230P and extension hole 165P. See FIGS. 23 and 24. Note that only compression screw 235A is shown in FIG. 23 due to the angle of view. Significantly, the compression screws engage bone on both sides of the osteotomy cut and, as the compression screws 235A, 235B are tightened, the compression screws draw the bone on both sides of the osteotomy closed, against the wedge-shaped implant.

Furthermore, the closely perpendicular relationship between the osteotomy plane and the compression screws allows for fixation to be maintained with screws in tension rather than in bending. The threads on either end of each compression screw also distribute shear load on the bone more evenly than a conventional locking plate-and-screw fixation that bears load on bone perpendicular to the axes of the screws. Fixation may also be enhanced by incorporating a small washer or plate of metal or plastic between each compression screw head and bone. The washer or plate may be self aligning to accommodate the bone geometry.

The controlled position and orientation of the compression screws help to locate the implant within the osteotomy. The compression screw axes are controlled through the use of osteotomy guide 100, which interfaces with the instrumentation which is aligned to anatomical features of the distal femur.

MODIFICATIONS

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A method for performing an open wedge, low femoral osteotomy comprising:
    defining an osteotomy plane in a femur, wherein the osteotomy plane terminates at a hinge pin axis;
    positioning at least one drill guide hole with an axis such that the drill guide hole axis intersects the osteotomy plane;
    deploying a hinge pin within the femur so that the hinge pin extends anterior-to-posterior, parallel to the sagittal plane of the patient;
    forming at least one guide hole in the femur along the drill guide hole axis;
    forming an osteotomy cut through the femur along the osteotomy plane, wherein the osteotomy cut substantially contacts the hinge pin;
    opening the femur along the osteotomy cut so as to form a wedge-shaped opening in the femur;
    positioning an osteotomy implant within the wedge-shaped opening in the femur; securing the osteotomy implant within the wedge-shaped opening in the femur; and wherein the osteotomy implant is secured within the wedge-shaped opening in the femur by passing a screw through the at least one guide hole in the femur and into the implant.

2. A method according to claim 1 wherein the hinge pin is positioned in the femur by passing the hinge pin through an anterior tissue shield, through the femur, and into a posterior tissue shield.

3. A method according to claim 1 wherein the osteotomy cut is formed in the femur by positioning anterior and posterior tissue shields on anterior and posterior sides of the femur, respectively, with a cutting guide being connected to the anterior and posterior tissue shields, and with the cutting guide presenting a cutting slot aligned with the hinge pin.

4. A method according to claim 1 wherein the screw passes through the femur on one side of the wedge-shaped opening, through the implant, and into the femur on the other side of the wedge-shaped opening.

5. A method according to claim 1 wherein the screw comprises a compression screw.

6. A method according to claim 1 wherein the osteotomy implant comprises a pre-formed hole for receiving the screw.

7. A method according to claim 1 wherein the screw is received in a hole which is formed in the implant after the implant has been positioned in the wedge-shaped opening.

8. A method according to claim 3 wherein the anterior tissue shield, the hinge pin and the posterior tissue shield together form a safety cage during formation of the osteotomy cut.

9. A method according to claim 1, wherein the at least one guide hole is formed distal to the osteotomy plane.

10. A method according to claim 9 further comprising forming at least one extension hole along the drill guide hole axis such the at least one extension hole is substantially aligned with the at least one guide hole, proximal to the osteotomy plane.

11. A method according to claim 1, wherein the osteotomy implant has at least one implant hole arranged such that when the implant is positioned in the femur, the at least one implant hole substantially aligns with the at least one guide hole.

* * * * *